United States Patent [19]
Bowden et al.

[11] Patent Number: 6,025,497
[45] Date of Patent: Feb. 15, 2000

[54] PROCESSES FOR THE PRODUCTION OF 5-CHLORO-2-(4,4-DIFLUOROBUT-3-ENYLSULPHONYL)THIAZOLE

[75] Inventors: Martin Charles Bowden, Brighouse; Stephen Martin Brown, Huddersfield, both of United Kingdom

[73] Assignee: Zeneca Limited, United Kingdom

[21] Appl. No.: 09/066,099

[22] Filed: Apr. 23, 1998

[30] Foreign Application Priority Data

Apr. 24, 1997 [GB] United Kingdom .................... 9708280

[51] Int. Cl.$^7$ .................................................. C07D 277/36
[52] U.S. Cl. .............................................................. 548/186
[58] Field of Search ................................................ 548/186

[56] References Cited

FOREIGN PATENT DOCUMENTS

WO95/24403  9/1995  WIPO .

*Primary Examiner*—Laura L. Stockton
*Attorney, Agent, or Firm*—Dianne Burkhard

[57] ABSTRACT

5-Chloro-2-(4,4-difluorobutenylthio)thiazole is prepared from 2-mercaptothiazole by a multistep process involving S-alkylation, chlorination and dehydrochlorination and is converted by oxidation to the corresponding sulfone which is useful as an agricultural nematicide.

13 Claims, No Drawings

PROCESSES FOR THE PRODUCTION OF 5-CHLORO-2-(4,4-DIFLUOROBUT-3-ENYLSULPHONYL)THIAZOLE

This invention relates to a process for preparing certain thiazole derivatives and to novel intermediates for use in the process.

International Patent Application Publication No. WO95/24403 discloses a class of compounds of formula:

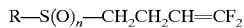

R—S(O)$_n$—CH$_2$CH$_2$CH=CF$_2$ wherein R represents an optionally substituted heterocyclic group selected from furyl, thienyl, isoxazolyl, isothiazolyl, oxazolyl, thiazolyl, imidazolyl, pyrazolyl, oxadiazolyl, thiadiazolyl, tetrazolyl, pyridyl, pyazinyl, pyridazinyl, and triazinyl groups, and n is zero or 1 or 2, said compounds having utility as pesticides and particularly as nematicides. Amongst these compounds those wherein R represents a chloro-substituted thiazolyl group and n is 2 are particularly useful as agricultural nematicides including specifically the compound 5-chloro-2-(4,4-difluorobut-3-enylsulphonyl) thiazole, of formula:

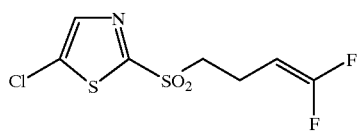

(I)

(hereinafter called "Compound (I)").

The preparation of Compound I as disclosed in WO95/24403 involves the reaction of 2-mercaptothiazole with 1,4-dibromo-1,1,2-trifluorobutane to give 4-bromo-3,4,4-trifluorobutylthiothiazole. At a later stage in the preparation the difluorobutenyl moiety is generated by debromofluorination using metallic zinc. Although this process was used in the laboratory to make the first sample of Compound I it is not suitable for large scale manufacture because 1,4-dibromo-1,1,2-trifluorobutane is not readily available and the use of metallic zinc in large scale manufacture is potentially hazardous. It was therefore necessary to devise an alternative process suitable for large scale manufacture which avoided the use of 1,4-dibromo-1,1,2-trifluorobutane and also avoided the use of metallic zinc.

Any process to prepare Compound I from 2-mercaptothiazole must involve the following elements:

(1) introduction of the 5-chloro substituent—"chlorination"

(2) introduction of the 4,4-difluorobutenyl group—"alkenylation", and (3) oxidation of the sulfur atom in the side chain—"oxidation"

In addition in the case of the alkenylation there exists the possibility of introducing the double bond by the use of a reactant already containing it—"direct alkenylation", as well as the possibility using a saturated reactant and generating the double bond at a later stage by an elimination reaction, ie "alkylation-elimination". It will also be appreciated that other elements of the process might be introduced in between the "alkylation" and "elimination" steps.

In considering the requirements of the process for making Compound I using the "direct alkenylation" approach there are in essence three different possible sequences, which may be summarised as follows:

(a) chlorination-alkenylation-oxidation
(b) alkenylation-oxidation-chlorination
(c) alkenylation-chlorination-oxidation and using the "alkylation-elimination" approach there are eight different possible sequences, thus:

(d) chlorination-alkylation-elimination-oxidation
(e) chlorination-alkylation-oxidation-elimination
(f) alkylation-chlorination-oxidation-elimination
(g) alkylation-chlorination-elimination-oxidation
(h) alkylation-elimination-chlorination-oxidation
(i) alkylation-elimination-oxidation-chlorination
(j) alkylation-oxidation-chlorination-elimination
(k) alkylation-oxidation-elimination-chlorination.

It will be readily appreciated that where a process involves several different transformations it is not possible to predict what effect the order in which the transformations occur has on the overall efficiency of the process.

The present invention provides a multi-stage process for the preparation of Compound (I) in good yield which is suitable for manufacture in so far as it avoids the use of metallic zinc and 1,4-dibromo-1,1,2-trifluorobutane.

Accordingly the invention provides a process for preparing a compound of formula:

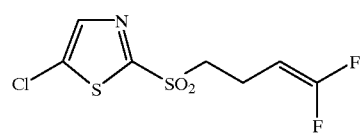

(I)

which comprises the steps of (a) reacting 2-mercaptothiazole with a compound of formula:

X—CH$_2$CH$_2$CH$_2$CClF$_2$ (II)

where X represents a readily displaceable leaving group to obtain a compound of formula:

(III)

and thereafter either (b)

(i) reacting said compound of formula (III) with a chlorinating agent to obtain a compound of formula:

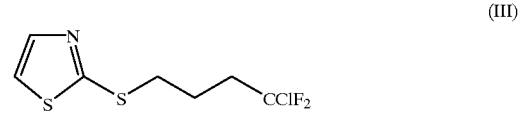

(IV)

and (ii) reacting said compound of formula (IV) with a dehydrochlorination agent selected from alkali metal carbonates and amines to obtain a compound of formula:

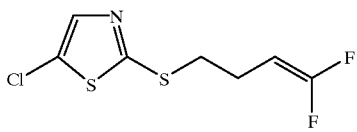
(V)

or (c)

(i) reacting said compound of formula (III) with a dehydrochlorination agent selected from alkali metal carbonates and amines to obtain a compound of formula:

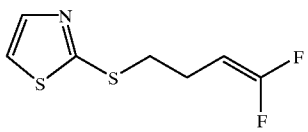
(VI)

and (ii) reacting said compound of formula (VI) with a chlorinating agent to obtain a compound of formula (V), and (d) reacting said compound of formula (V) with an oxidising agent to obtain the compound of formula (I).

Preferably the compound of formula (II) is 1,4-dichloro-1,1-difluorobutane. The preparation of this compound is described in United Kingdom Patent Application Publication no. 2304713.

The compound of formula (III), which is 2-(4-chloro-4,4-difluorobutylthio)thiazole, and the compound of formula (IV), which is 5-chloro-2-(4-chloro-4,4-difluorobutylthio)thiazole, are new. In a further aspect the present invention provides 2-(4-chloro-4,4-difluorobutylthio)thiazole and 5-chloro-2-(4-chloro-4,4-difluorobutylthio)thiazole which are useful as intermediates in the process of the invention. Identifying characteristics of these compounds are given in the examples hereinafter.

Within the overall sequence of the invention process there are preferred conditions under which each stage may be carried out. Thus step (a) is preferably conducted in the presence of a base and solvent or diluent. Suitable bases include alkali metal hydroxides such as sodium or potassium hydroxides, alkali metal carbonates, such as sodium and potassium carbonates, and suitable solvents include ketones, such as acetone, methyl isobutyl ketone and cyclohexanone, esters such as methyl acetate, and polar aprotic solvents such as dimethylformamide and dimethylacetamide. Particularly preferred conditions for step (a) involve the use of solid potassium carbonate in combination with a ketonic solvent.

The preferred conditions for the chlorination stage, step (b)(i) or step (c)(ii), involve the use of sulfuryl chloride as a chlorination agent. The chlorination may be conducted in the presence of a solvent which may for example be a chlorinated hydrocarbon such as chloroform, or a polar aprotic solvent such as dimethylformamide and dimethylacetamide. Particularly preferred conditions involve the use sulfuryl chloride in combination with a polar aprotic solvent.

The elimination steps (b)(ii) and (c)(i) involve the dehydrochlorination of the chlorodifluorobutyl moiety to generate the double bond. This may be accomplished by use of a base which may be an amine, such as a trialkylamine including for example, triethylamine, or a heterocyclic base such as pyridine or it may be an inorganic base such as an alkali metal carbonate for example sodium or potassium carbonate. It is also preferred to carry out this step in the presence of a solvent which may be an alkanol such as methanol or isopropanol, an ester such as ethyl acetate, or a polar aprotic solvent such as dimethylformamide or dimethylacetamide. Particularly preferred conditions involve the use of solid potassium carbonate in the presence of a polar aprotic solvent.

Suitable oxidising agents for use in step (d) include for example, hydrogen peroxide, and peracids, such as peracetic acid, which may be generated in situ by adding hydrogen peroxide to glacial acetic acid.

The efficacy of each stage of the invention process can also be improved by conducting it within an an appropriate temperate range. It is preferred to conduct each stage at an elevated temperature, as follows: step (a) from 50° C. to the reflux temperature, preferably the reflux temperature; step (b)(i) and step (c)(ii) from 40 to 70° C., preferably ca. 45° C. step (b)(ii) and step (c)(i) from 60 to 130° C., preferably ca. 120° C.; and step (d) from 45 to 75° C., preferably 55 to 60° C.

Each of the stages of the invention process is preferably conducted at the ambient atmospheric pressure.

The process of the invention is illustrated by the following examples.

EXAMPLE 1

This Example illustrates the preparation of 2-(4-chloro-4,4-difluorobutylthio)thiazole Solid anhydrous potassium carbonate (9.33 g) was added in two portions to a stirred mixture of 2-mercaptothiazole (7.90 g), 1,4-dichloro- 1,1-difluorobutane (9.70 g) and acetone (150 ml) under a nitrogen atmosphere, and the resultant mixture heated at the reflux temperature for 4 hours. After cooling to the ambient temperature the solid component was removed by filtration and washed with acetone (2×50 ml) and the combined washings and filtrate concentrated by evaporation of the solvent under reduced pressure. Diethyl ether (150 ml) was added to the residue and the resultant solution washed with aqueous potassium carbonate solution (2×100 ml) and with water (100 ml). After drying over anhydrous magnesium sulfate the solution was concentrated by removal of the solvent by evaporation under reduced pressure to yield 2-(4-chloro-4,4-difluorobutylthio)thiazole (13.98 g, 94%).

$^1$Hnmr (CDCl$_3$): 2.00–2.20 (m, 2H, C$\underline{H}$2), 2.30–2.60 (m, 2H, C$\underline{H}$2CF2Cl), 3.30 (t, 2H, C$\underline{H}$2S), 7.25 (d, 1H, Ar$\underline{H}$), 7.65 (d, 1H, Ar$\underline{H}$).

GCMS: 243 (M$^+$), 208 (M—Cl)$^+$, 174 (M—CH2CF2Cl)$^+$, 144, 130, 117.

EXAMPLE 2

This Example illustrates the preparation of 5-chloro-2-(4-chloro-4,4-difluorobutylthio)thiazole.

A solution of sulfuryl chloride (2.94 g) and chloroform (10 ml) was added dropwise over a period of one hour to a stirred mixture of 2-(4-chloro-4,4-difluorobutylthio)thiazole (4.85 g), and dimethylacetamide (47 g) maintained at 45° C. under a nitrogen atmosphere and the resultant mixture stirred for a further one hour. A further aliquot of sulfuryl chloride (0.58 g) dissolved in chloroform (5.0 ml) was then added over 45 minutes and the mixture stirred for a further 30 minutes. After cooling the reaction mixture to the ambient temperature water (50 ml) was added and the mixture extracted with hexane (3×50 ml). The hexane solution was washed with water (50 ml), saturated aqueous sodium bicarbonate solution (50 ml) and water (50 ml) and then dried over anhydrous magnesium sulfate. Removal of the solvent by evaporation under reduced pressure yielded of 5-chloro-2-(4-chloro-4,4-difluorobutylthio)thiazole (5.0 g, 87%).

$^1$H nmr (CDCl$_3$): 2.00–2.20 (m, 2H, C$\underline{H}$2), 2.40–2.60 (m, 2H, C$\underline{H}$2CF2Cl), 3.30, t, 2H, C$\underline{H}$2S), 7.45 (s, 1H, Ar$\underline{H}$).
$^{13}$C nmr (CDCl$_3$): 23(s), 33(s), 41(t), 126(s), 130(t), 141(s), 162(s).
MS: 277 (M$^+$), 242, 208, 178, 165, 151.

EXAMPLE 3

This Example illustrates the preparation of 5-chloro-2-(4, 4-difluorobut-3-enylthio)thiazole.

A mixture of 5-chloro-2-(4-chloro-4,4-difluorobutylthio) thiazole (4.75 g), powdered potassium carbonate (3.47 g) and dimethylacetamide (47 g) was maintained at a temperature of 120° C. under a nitrogen atmosphere for a period of 18 hours and then cooled to the ambient temperature. Water (50 ml) was added and the mixture extracted with hexane (3×50 ml). The combined extracts were washed with water (2×50 ml), dried over anhydrous magnesium sulfate and concentrated by evaporation of the solvent under reduced pressure to yield of 5-chloro-2-(4,4-difluorobut-3-enylthio) thiazole (3.65 g, 86%).
$^1$H nmr (CDCl$_3$): 2.35–2.55 (m, 2H, C$\underline{H}$2), 3.25, t, 2H, C$\underline{H}$2S), 4.25 (dt, 1$\underline{H}$, C$\underline{H}$=CF2), 7.45 (s, 1H, Ar$\underline{H}$).
$^{13}$C nmr (CDCl$_3$): 23(s), 34(s), 77(t), 125(s), 142(s), 157(t), 163(s).
MS: 241(M$^+$), 208, 164, 151.
IR (cm$^{-1}$): 1750 (C=CF$_2$).

EXAMPLE 4

This Example illustrates the preparation of 2-(4,4-difluorobut-3-enylthio)thiazole.

A mixture of 2-(4-chloro-4,4-difluorobutylthio)thiazole (1.01 g), powdered potassium carbonate (0.85 g) and dimethylacetamide (10 ml) was maintained at a temperature of 120° C. under a nitrogen atmosphere for a period of 18 hours and then cooled to the ambient temperature. Water (20 ml) was added and the mixture extracted with hexane (3×20 ml). The combined extracts were washed with water (2×20 ml), dried over anhydrous magnesium sulfate and concentrated by evaporation of the solvent under reduced pressure to yield of 2-(4,4-difluorobut-3-nylthio)thiazole (0.90 g, 98%).
$^1$H nmr (CDCl$_3$): 2.40–2.55 (m, 2H, C$\underline{H}$2), 3.25, t, 2H, C$\underline{H}$2S), 4.30 (dt, 1$\underline{H}$, C$\underline{H}$=CF2), 7.25, (d, 1$\underline{H}$, Ar$\underline{H}$).
MS: 207(M$^+$), 174, 117.
IR (cm$^{-1}$): 1750 (C=CF$_2$).

EXAMPLE 5

This Example illustrates the preparation of 5-chloro-2-(4, 4-difluorobut-3-enylthio)thiazole.

A solution of sulfuryl chloride (0.66 g) and chloroform (2.0 ml) was added dropwise over a period of 1.5 hour to a stirred mixture of 2-(4,4-difluorobut-3-enylthio)thiazole (1.01 g), and dimethylformamide (10 ml) maintained at 45° C. under a nitrogen atmosphere and the resultant mixture stirred for a further 2.5 hour. A further aliquot of sulfuryl chloride (0.07 g) dissolved in chloroform (1.0 ml) was then added over 15 minutes and the mixture stirred at 45° C. for 16 hours. A third portion of sulfuryl chloride (0.07 g) in chloroform (1.0 ml) was added over 30 minutes with the mixture being stirred for a further 2 hours, following which a final portion of the sulfuryl chloride (0.07 g) in chloroform (1.0 ml) was added and the mixture stirred for a final period of 30 minutes. After cooling the reaction mixture to the ambient temperature water (20 ml) was added and the mixture extracted with hexane (25 ml). The pH of the aqueous portion was adjusted to pH7 with 10% sodium hydroxide solution and extracted with hexane (25 ml). The combined hexane extracts were washed with water (2×20 ml) and then dried over anhydrous magnesium sulfate. Removal of the solvent by evaporation under reduced pressure yielded of 5-chloro-2-(4,4-difluorobut-3-enylthio) thiazole (1.13 g, 88%), identical to the product of Example 3.

EXAMPLE 6

This Example illustrates the preparation of 5-chloro-2-(4, 4-difluorobut-3-enylsulfonyl)thiazole.

Hydrogen peroxide (0.77 g) was added to a mixture of 5-chloro-2-(4,4-difluorobut-3-enylthio)thiazole (1.94 g) and glacial acetic acid (21 g) at a temperature of 55–60° C. and the resultant mixture maintained at this temperature for 6 hours. After cooling the mixture to 5° C. and adding sufficient 47% sodium hydroxide solution to adjust the pH to 6 the mixture was diluted with water (20 ml) and extracted with chloroform (3×20 ml). The combined extracts were washed with water (20 ml), sodium bisulfite solution (20 ml), and water (20 ml) and dried over anhydrous magnesium sulfate. Removal of the solvent by evaporation under reduced pressure yielded 5-chloro-2-(4,4-difluorobut-3-enylsulfonyl)thiazole (1.95 g, 82%).
$^1$H nmr (CDCl$_3$): 2.50–2.70 (m, 2H, C$\underline{H}$2), 3.45, t, 2H, C$\underline{H}$2SO2), 4.25 (dt, 1$\underline{H}$, C$\underline{H}$=CF2), 7.85 (s, 1$\underline{H}$, ArH).
MS: 208(M$^+$), 188, 170, 119, 90.
IR (cm$^{-1}$): 1138 (SO$_2$), 1170 (SO$_2$), 1330 (SO$_2$), 1750 (C=CF$_2$).

The through yield of 5-chloro-2-(4,4-difluorobut-3-enylsulfonyl)thiazole with respect to 2-mercaptothiazole by the process of the invention illustrated by Examples 1, 2, 3 and 6 is 57.7%. The through yield with respect to 2-mercaptothiazole by the process of the invention represented by Examples 1, 4, 5 and 6 is 66.5%.

We claim:
1. A process for preparing a compound of formula:

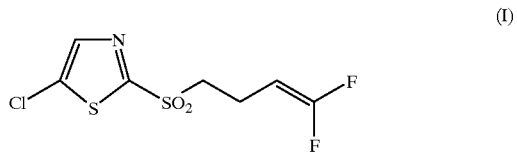

which comprises the steps of
(a) reacting 2-mercaptothiazole with a compound of formula:

where X represents a readily displaceable leaving group to obtain a compound of formula:

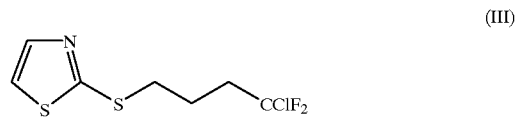

and thereafter either (b)
(i) reacting said compound of formula (III) with a chlorinating agent to obtain a compound of formula:

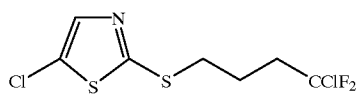

and (ii) reacting said compound of formula (IV) with a dehydrochlorination agent selected from alkali metal carbonates and amines to obtain a compound of formula:

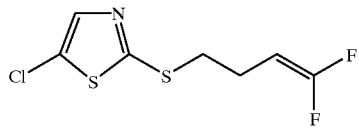

or (c)
(i) reacting said compound of formula (III) with a dehydrochlorination agent selected from alkali metal carbonates and amines to obtain a compound of formula:

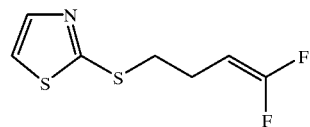

and (ii) reacting said compound of formula (VI) with a chlorinating agent to obtain a compound of formula (V), and (d) reacting said compound of formula (V) with an oxidising agent to obtain the compound of formula (I).

2. A process according to claim 1 wherein the compound of formula (II) is 1,4-dichloro-1,1-difluorobutane.

3. A process according to claim 1 wherein step (a) is conducted in the presence of a base and a solvent.

4. A process according to claim 3 wherein the base is solid potassium carbonate.

5. A process according to claim 1 wherein the chlorination agent is sulfuryl chloride.

6. A process according to claim 1 wherein the dehydrochlorination agent is an alkali metal carbonate.

7. A process according to claim 1 wherein the oxidising agent is an organic peracid.

8. A process according to claim 1 wherein steps (b)(i) and (c)(ii) are carried out in the presence of a polar aprotic solvent.

9. A process according to claim 1 wherein steps (b)(ii) and (c)(i) are carried out in the presence of a polar aprotic solvent.

10. A process according to claim 8 in which the polar aprotic solvent is selected from dimethylformamide and dimethylacetamide.

11. A process according to claim 9 in which the polar aprotic solvent is selected from dimethylformamide and dimethylacetamide.

12. A process according to claim 1 consisting of steps (a), (b)(i), (b)(ii) and (d).

13. A process according to claim 1 consisting of steps (a), (c)(i), (c)(ii) and (d).

* * * * *